United States Patent [19]

Fryer et al.

[11] 4,032,535
[45] June 28, 1977

[54] TRIAZOLOBENZODIAZEPINES

[75] Inventors: Rodney Ian Fryer, North Caldwell; Armin Walser, West Caldwell, both of N.J.

[73] Assignee: Hoffmann-La Roche Inc., Nutley, N.J.

[22] Filed: Aug. 18, 1976

[21] Appl. No.: 715,606

Related U.S. Application Data

[63] Continuation of Ser. No. 419,563, Nov. 28, 1973, abandoned.

[52] U.S. Cl. .......................... 260/308 R; 260/143; 424/269
[51] Int. Cl.[2] ...................................... C07D 487/14
[58] Field of Search .............................. 260/308 R

[56] References Cited

OTHER PUBLICATIONS

Collins–C.A. 79,52018n (1973).

*Primary Examiner*—Raymond V. Rush
*Attorney, Agent, or Firm*—Samuel L. Welt; George M. Gould; Frank P. Hoffman

[57] ABSTRACT

6-Phenyl-S-triazolo[4,3-a][1,4]benzodiazepines bearing in the 8-position a hydroxyamino or azoxy substituent are disclosed together with processes for preparing these compounds and intermediates used in these processes. These triazolobenzodiazepines are useful as muscle relaxant, anti-convulsant and sedative agents.

2 Claims, No Drawings

TRIAZOLOBENZODIAZEPINES

This is a continuation of application Ser. No. 419,563 filed Nov. 28, 1973, now abandoned.

DETAILED DESCRIPTION OF THE INVENTION

The present invention relates to novel triazolobenzodiazepine derivatives bearing a hydroxyamino or azoxy substituent in the 8-position. This invention further comprehends processes for making these novel benzodiazepines and novel intermediates employed in these processes.

More specifically, the compounds of the present invention are selected from the group consisting of compounds of the formula

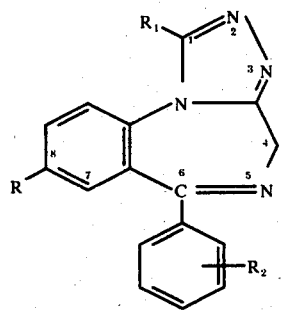

wherein R is selected from the group consisting of -NHOH and

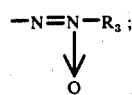

$R_1$ signifies hydrogen or lower alkyl; $R_2$ signifies hydrogen or halogen; $R_3$ signifies lower alkyl and the pharmaceutically acceptable acid addition salts thereof.

As used herein the term "lower alkyl" refers to straight and branched chain hydrocarbon groups containing from 1 to 7, preferably from 1 to 4 carbon atoms such as, for example methyl, ethyl, propyl, isopropyl, isobutyl, butyl and the like. The term "halogen" refers to all four forms thereof, ie. bromine, chlorine, fluorine and iodine.

Preferred among the compounds falling within the scope of formula I above are those wherein R signifies hydroxyamino, i.e. compounds of the formula

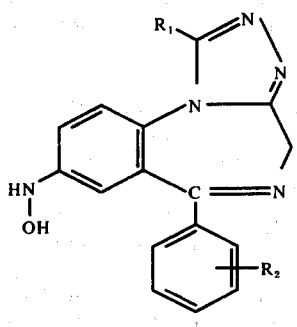

wherein $R_1$ and $R_2$ are as described above and the pharmaceutically acceptable acid addition salts thereof.

Also preferred among the compounds falling within the scope of formula I above are those wherein the R substituent is an azoxy group, i.e. compounds of the formula

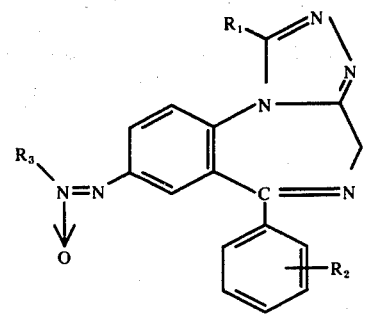

wherein $R_1$ through $R_3$ are as described above and the pharmaceutically acceptable acid addition salts thereof.

When the $R_1$ substituent signifies lower alkyl, methyl is preferred. When the $R_2$ substituent is halogen, chlorine and fluorine are preferred and this substituent is preferably located at the ortho position of the 6-phenyl ring. The preferred lower alkyl group for the $R_3$ substituent is methyl.

Representative of the compounds of formula I above are: 6-(2-chlorophenyl)-8-hydroxyamino-1-methyl-4H-S-triazolo[4,3-a][1,4]benzodiazepine and 6-(2-Chlorophenyl)-1-methyl-8-(N-methyl-N-oxyazo)-4H-s-triazolo[4,5][1,4]benzodiazepine.

The compounds of formula I above wherein the R substituent is a hydroxyamino group, i.e. the compounds of formula Ia above are prepared by the selective reduction of the corresponding 8-nitrotriazolobenzodiazepines of the formula

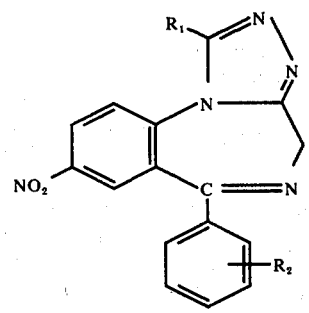

wherein $R_1$ and $R_2$ are as described above.

The 8-nitrotriazolobenzodiazepine derivatives of formula II above are known compounds or can be prepared in analogy to the preparation of the known material. The reduction of the 8-nitro group to the desired hydroxyamino group is accomplished by selective chemical or catalytic reducing systems. Suitable reducing systems for the present purposes include zinc in ammonium chloride and stannous chloride in a buffered system. Acetate, citrate or phosphate buffers are suitable with sodium acetate being preferred. This reduction is preferably effected in the presence of an inert organic solvent. Representative of the solvents that can be employed are alcohols such as methanol, ethanol and the like, water, ethers such as tetrahydrofuran, hydrocarbons such as hexane and the like, chlorinated hydrocarbons such as chloroform, methylene chloride and the like, acetone, dimethylformamide and dimethylsulfoxide. Temperature is not critical to this process aspect so that temperatures above or below room temperature can be employed with room temperature being preferred.

The compounds of formula I above wherein the R substituent is an azoxy group, ie. the compounds of formula Ib above may be prepared by first converting the 8-hydroxyamino derivative of formula Ia to the corresponding 8-nitrosobenzodiazepine of the formula

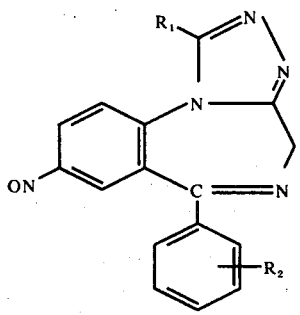   III wherein $R_1$ and $R_2$ are as described above.

The 8-nitroso derivatives of formula III above may be prepared by the oxidation of the corresponding 8-hydroxyaminotriazolobenzodiazepines. This oxidation is effected by treating the compounds of formula Ia above with an oxidizing agent. Suitable oxidizing agents for the purposes of this process aspect include ferric chloride, manganese dioxide, cupric chloride and the like with manganese dioxide being preferred. This oxidation is preferably effected in the presence of an inert organic solvent. Suitable solvents include hydrocarbons such as hexane, ethers such as tetrahydrofuran and chlorinated hydrocarbons such as chloroform and methylene chloride. Temperature is not critical to this process aspect and thus the reaction is expediently effected at room temperature.

The 8-nitroso triazolobenzodiazepines of formula III above are novel and as such form a part of the present invention. These compounds, in addition to being useful as intermediates in the preparation of the compounds of formula Ia, also themselves exhibit sedative, muscle relaxant and anti-convulsant activity.

The 8-azoxy derivatives of formula Ib above may then be prepared by reacting the corresponding 8-nitrosobenzodiazepine of formula III with a lower alkyl hydroxylamine of the formula $$R_3 - NHOH \qquad IV$$

wherein $R_3$ is as described above.

The reaction of the 8-nitrosotriazolobenzodiazepine of formula III with the lower alkyl hydroxylamine of formula IV is preferably effected in the presence of an inert organic solvent. Suitable solvents for this reaction include hydrocarbons such as hexane, chlorinated hydrocarbons such as chloroform and methylene chloride, alcohols such as methanol, ethanol, propanol and the like, ethers such as tetrahydrofuran and dimethylformamide. Temperature is not critical to this process aspect and thus temperatures from room temperature to the reflux temperature of the reaction medium can be employed with the reflux temperature being preferred. Representative of the compounds of formula IV suitable for the purposes of the present invention are methylhydroxylamine, ethylhydroxylamine, propylhydroxylamine and the like.

The compounds of formulae I and III above form pharmaceutically acceptable acid addition salts with organic and inorganic acids, thus the compounds of the present invention form pharmaceutically acceptable acid addition salts with inorganic acids such as hydrohalic acids, for example, hydrochloric acid and hydrobromic acid and with organic acids such as tartaric acid, citric acid, camphorsulfonic acid, ethanesulfonic acid, toluenesulfonic acid salicyclic acid, ascrobic acid, maleic acid, succinic acid, formic acid, acetic acid and the like.

The compounds of formulae I and III above as well as their pharmaceutically acceptable acid addition salts are useful as anti-convulsant, muscle relaxant and sedative agents. Thus, the compounds of the present invention and their pharmaceutically acceptable salts can be used as medicaments. For example, they can be used in the form of pharmaceutical preparations which contain them or their salts in ad-mixture with a pharmaceutical organic or inorganic carrier material which is suitable for enteral or parenteral application such as, for example, water, gelatin, lactose, starches, magnesium sterate, talc, vegetable oils, gum arabic, polyalkyleneglycols, vaseline, etc. The pharmaceutical preparations can be prepared in solid form (e.g. as tablets, dragees, suppositories, capsules) or in liquid form (e.g. as solutions, suspensions or emulsions). They may be sterilized and/or contain additives such as preserving, stabilizing, wetting or emulsifying agents, salts for varying the osmotic pressure or buffers. They can also contain other therapeutically valuable substances.

The compounds of formulae I and III above or their pharmaceutically acceptable salts can be administered at dosages adjusted to individual requirements and fitted to the pharmaceutical exigencies of the situation. Convenient pharmaceutical dosages are in the range of from about 2 mg. to about 200 mg. per day.

The useful anticonvulsant activity of the compounds of formulae I and III above is shown in warm blooded animals utilizing the standard antimetrazole test. This test was carried out according to the method of Everett and Richard (J.P.E.T., 81: 402, 1944). The $ED_{50}$ was calculated as the dose which would prevent convulsions in 50% of the mice tested after administration of 125 mg/kg of pentylenetetrazole by the subcutaneous route. Following these test procedures 6-(2-Chlorophenyl)-8-hydroxyamino-1-methyl-4H-S-triazolo[4,3-a][1,4]benzodiazepine (Compound A), 6-(2-Chlorophenyl)-1-methyl-8-nitroso-4H-s-triazolo[4,3-a][1,4]benzodiazepine (Compound B) and 6-(2-Chlorophenyl)-1-methyl-8-(N-methyl-N-oxyazo)-4H-s-triazolo[4,5-a][1,4]benzodiazepine (Compound C) show an $ED_{50}$ of 74 + 15, 4.0 + 1.3 and 1.65 + 0.2 mg/kg respectively, indicating that these compounds are useful as anti-convulsant agents.

The sedative and muscle relaxant activity of the compounds of formulae I and III above are shown using the standard foot shock test. In this test a pair of mice is confined under a 1 liter beaker placed on a grid which presents shock to the feet. At least five fighting episodes are elicited in a two minute period. Pairs of mice are marked and pretreated 1 hour prior to a second shock. Logarithmic dose intervals are utilized up to a maximum of 100 mg/kg. At the 100% blocking dose, three out of three pairs must be blocked from fighting.

The measurements are made at the dose level at which 100% blocking is observed and the results are expressed as the dose in mg/kg ($PD_{50}$) which blocks the fighting response for 1-hour. Following these test procedures, Compound A exhibits a $PD_{50}$ of 10 mg/kg, Compound B exhibits a $PD_{50}$ of 10 mg/kg and Compound C exhibits a $PD_{50}$ of 5 mg/kg, indicating that these compounds exhibit sedative and muscle-relaxant activity.

The following examples are illustrative of the present invention. All temperatures are given in degrees Centigrade.

EXAMPLE 1

Preparation of
6-(2-Chlorophenyl)-8-hydroxyamino-1-methyl-4H-S-triazolo[4,3-a][1,4]benzodiazepine A mixture of 3.55g (0.01 m) of 6-(2-chlorophenyl)-1-methyl-8-nitro-4H-s-triazolo[4,3-a][1,4]benzodiazepine, 200 ml of tetrahydrofuran, 100 ml of methanol, 13.6 g of sodium acetate trihydrate and 12 g of stannous chloride dihydrate was stirred at room temperature for 1 hr under nitrogen atmosphere. After addition of 5 ml of conc. aqueous ammonia the inorganic material was separated by filtration over celite. The filter cake was washed with 500 ml of methylene chloride containing 20% of ethanol. The filtrate was evaporated and the residue was stirred with 100 ml of water and 30 ml of methylene chloride. The crystalline material was collected and washed successively with water, ethanol and ether to yield the above-named product. For analysis it was recrystallized from tetrahydrofuran/methanol, mp. 276°–278° dec.

EXAMPLE 2

Preparation of
6-(2-Chlorophenyl)-1-methyl-8-nitroso-4H-s-triazolo[4,3-a][1,4]-benzodiazepine Manganese dioxide, 20g, was added to a suspension of 2 g of 6-(2-chlorophenyl)-8-hydroxyamino-1-methyl-4H-s-triazolo-[4,3-a][1,4]benzodiazepine in 1 1 of methylene chloride. After stirring for 3 hr at room temperature the manganese dioxide was separated by filtration over celite. The filtrate was evaporated and the residue was crystallized from methylene chloride/ether to yield the above-named product, with m.p. 190°–195° dec. For analysis it was recrystallized from ethanol/ether.

EXAMPLE 3

Preparation of
6-(2-Chlorophenyl)-1-methyl-8-(N-methyl-N-oxyazo)-4H-s-triazolo[4,5-a][1,4]benzodiazepine A mixture of 1g of 6-(2-chloropenyl)-1-methyl-8-nitroso-4H-s-triazolo[4,3-a][1,4]benzodiazepine, 1g of methylhydroxyamine, 1.5g of sodium acetate and 30 ml of ethanol was heated to 40°–50° for 5 min. The ethanol was removed under reduced pressure and the residue was partitioned between methylene chloride and 10% aqueous sodium carbonate solution. The organic layer was separated, dried over sodium sulfate and evaporated. The residue was chromatographed over 30g of silica gel (Merck, 70–230 mesh) using 10% (v/v) of ethanol in methylene chloride. Clean fractions were combined and evaporated. Crystallization from ethyl acetate yielded the above-named product. Since no solvent free crystals were obtained with a variety of solvents the product was characterized as a solvent. Recrystallization from 2-propanol yielded crystals containing one quarter mole of solvent with m.p. 160°–165°.

EXAMPLE 4

| Capsule Formulation | Per Capsule |
|---|---|
| 6-(2-Chlorophenyl)-8-hydroxyamino-1-methyl-4H-S-triazolo[4,3-a][1,4]benzodiazepine | 50 mg |
| Lactose, USP | 125 mg |
| Corn Starch, USP | 30 mg |
| Talc, USP | 5 mg |
| Total Weight | 210 mg |

Procedure:
1. The drug was mixed with lactose and corn starch in a suitable mixer.
2. The mixture was further blended by passing through a Fitzpatrick Comminuting machine with a No. 1A screen with knives forward.
3. The blended powder was returned to the mixer, the talc added and blended thoroughly.
4. The mixture was filled into No. 4 hard shell gelatin capsules on a Parke Davis capsulating machine.

EXAMPLE 5

| Capsule Formulation | Per Capsule |
|---|---|
| 6-(2-Chlorophenyl)-8-hydroxyamino-1-methyl-4H-S-triazolo[4,3-a][1,4] benzodiazepine | 10 mg |
| Lactose | 158 mg |
| Corn Starch | 37 mg |
| Talc | 5 mg |
| Total Weight | 210 mg |

Procedure:
1. The drug was mixed with the lactose and corn starch in a suitable mixer.
2. The mixer was further blended by passing through a Fitzpatrick Comminuting machine with a No. 1A screen with knives forward.
3. The blended powder was returned to the mixer, and talc added and blended thoroughly. The mixture was then filled into No. 4 hard shell gelatin capsules on a Parke Davis capsulating machine. (Any similar type machine may be used).

EXAMPLE 6

| Tablet Formulation | Per Tablet |
|---|---|
| 6-(2-Chlorophenyl)-8-hydroxyamino-1-methyl-4H-S-triazolo[4,3-a][1,4] benzodiazepine | 25.00 mg |
| Lactose, USP | 64.50 mg |
| Corn Starch | 10.00 mg |
| Magnesium Stearate | 0.50 mg |
| Total Weight | 100.00 mg |

Procedure:
1. The drug was mixed with the lactose, corn starch and magnesium stearate in a suitable mixer.
2. The mixture was further blended by passing through a Fitzpatrick Comminuting machine fitted with a No. 1A screen with knives forward.
3. The mixed powders were slugged on a tablet compressing machine.

4. The slugs were comminuted to a mesh size (No. 16 screen) and mixed well.

5. The tablets were compressed at a tablet weight of 100 mg using tablet punches having a diameter of approximately one-fourth inch. (Tablets may be either flat or biconvex and may be scored if desired).

EXAMPLE 7

| Tablet Formulation | Per Tablet |
|---|---|
| 6-(2-Chlorophenyl)-8-hydroxyamino-1-methyl-4H-S-triazolo[4,3-a][1,4] benzodiazepine | 10.0 mg |
| Lactose | 113.5 mg |
| Corn Starch | 70.5 mg |
| Pregelatinized Corn Starch | 8.0 mg |
| Calcium Stearate | 3.0 mg |
| Total Weight | 205.0 mg |

Procedure:

1. The drug was mixed with the lactose, corn starch and pregelatinized corn starch in a suitable size mixer.

2. The mix was passed through a Fitzpatrick Comminuting machine fitted with No. 1A screen and with knives forward.

3. The mix was returned to the mixer and moistened with water to a thick paste. The moist mass was passed through a No. 12 screen and the moist granules were dried on paper lined trays at 110° F.

4. The dried granules were returned to the mixer, the calcium stearate was added, and mixed well.

5. The granules were compressed at a tablet weight of 200 mg using standard concave punches having a diameter of five-sixteenths inch.

We claim:

1. A compound of the formula

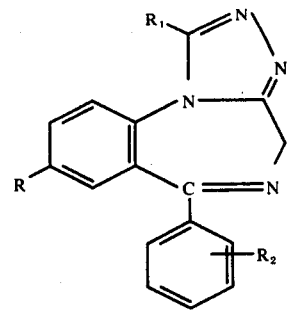

wherein R is —NHOH; $R_1$ signifies hydrogen or lower alkyl; $R_2$ signifies hydrogen or halogen; and the pharmaceutically acceptable acid addition salts thereof.

2. The compound of claim 1 of the formula 6-(2-chlorophenyl)-8-hydroxyamino-1-methyl-4H-s-triazolo[4,3-a][1,4]benzodiazepine.

* * * * *